United States Patent [19]

Duffett

[11] Plant 5,225

[45] May 1, 1984

[54] CHRYSANTHEMUM PLANT NAMED SPLENDOR

[75] Inventor: William E. Duffett, Salinas, Calif.

[73] Assignee: Yoder Brothers, Inc., Barberton, Ohio

[21] Appl. No.: 413,570

[22] Filed: Aug. 31, 1982

[51] Int. Cl.[3] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Koch

[57] ABSTRACT

A chrysanthemum plant named Splendor and characterized by the combined characteristics of flat capitulum form, daisy capitulum type; light lavender ray floret color; diameter across face of capitulum ranging from 145 to 160 mm. at maturity; uniform nine (9) week photoperiodic flowering response to short days; medium plant height when grown as a pinched, disbudded pot mum and upright branching pattern.

3 Drawing Figures

1

The present invention comprises a new and distinct cultivar of *Chrysanthemum morifolium,* Ramat., hereinafter referred to by the cultivar name Splendor.

Splendor is a product of a planned breeding program which had the objective of creating new chrysanthemum cultivars for pinched disbudded pot mum programs having daisy capitulum type, lavender floret color, 8 to 9 week flowering response and having the ability to produce commercially acceptable quality in year round programs. Such traits in combination were in need of improvement in previously available commercial cultivars.

Splendor was originated from a cross planned and executed by William E. Duffett in a controlled breeding program in Salinas, Calif. in 1977. The female parent was an unnamed lavender decorative (74282001) originated from a hybridization of Illini Trophy (commercially available) and a lavender decorative seedling (70029014). The male parent of Splendor was an unnamed lavender daisy seedling (76182022) originated from a cross between Sophisticate (U.S. Plant Pat. No. 3,944) and Gem (U.S. Plant Pat. No. 3,907), a light lavender daisy.

Splendor was discovered and selected as one flowering plant within the progeny of the stated cross by William E. Duffett on Aug. 16, 1978 in a controlled environment in Salinas, Calif.

The first act of asexual reproduction of Splendor was accomplished when vegetative cuttings were taken from the initial selection in November 1978 in a controlled environment in Salinas, Calif. by a technician working under formulations established and supervised by William E. Duffett. Horticultural examination of selected units initiated November 1979 has demonstrated that the combination of characteristics as herein disclosed for Splendor are firmly fixed and are retained through successive generations of asexual reproduction.

Splendor has not been observed under all possible environmental conditions. The phenotype may vary significantly with variations in environment such as temperature, light intensity and day length. The following observations, measurements and comparisons describe plants grown in Salinas, Calif. under greenhouse conditions which approximate those generally used in commercial practice.

The following traits have been repeatedly observed and are determined to be basic characteristics of Splendor which in combination distinguish this chrysanthemum as a new and distinct cultivar:

2

1. flat capitulum form;
2. daisy capitulum type;
3. light lavender ray floret color;
4. diameter across face of capitulum ranging from 145 to 160 mm. at maturity;
5. uniform nine (9) week photoperiodic flowering response to short days;
6. medium plant height (requiring 1–2 long day weeks prior to pinch and short days, and one to three applications of 2500 ppm B-9 SP after the onset of short days to attain a flowered plant height of 30 to 40 cm.); and
7. upright branching pattern.

The accompanying sheets depict typical foliage and inflorescence characteristics of Splendor. Sheet 1 is a color photograph of a plant of Splendor grown as a 4 cutting, 6" pinched, disbudded pot mum, with colors being as accurate as possible with renditions of this type. Sheet 2 is a black and white photograph of three views of the inflorescence of Splendor. Sheet 3 shows the top and bottom of the leaves of Splendor in three stages of growth (mature, intermediate and immature).

Of the many commercial cultivars known to the present inventor, the most similar in comparison to Splendor is Senorita (U.S. Plant Pat. No. 3,629). Reference is made to attached Chart A which compares certain characteristics of Splendor to those same characteristics of Senorita.

In comparison to Senorita, Splendor has longer form retention, more upright branching pattern, shorter plant height and shorter flowering response period. The ray floret color, capitulum form, capitulum type and diameter across face of capitulum of Splendor are similar to those same characteristics of Senorita. In addition, the reverse side of the ray florets of Senorita are hairy; those of Splendor are smooth.

In the following description, color references are made to The Royal Horticultural Society Color Chart. The color values were determined between 10:00 and 10:30 A.M. on June 1, 1982 under 150 foot-candle light intensity at Salinas, Calif.

CLASSIFICATION

Botanical: *Chrysanthemum morifolium,* Ramat., cv Splendor.

Commercial: Disbud daisy pot mum.

INFLORESCENCE

A. Capitulum

*Form.*—Flat.

*Type.*—Daisy.

*Diameter across face.*—145 to 160 mm.

B. Corolla of ray florets

*Color(General tonality from a distance of three meters).*—Light lavender.

*Color (abaxial).*—74B and 74C oxidizing to 75A to 75C.

*Color (adaxial).*—75B to 75D.

C. Corolla of disc florets

*Color (mature).*—1B.

*Color (immature).*—3A.

D. Reproductive organs

*Androecium.*—Present disc florets only; scant pollen.

*Gynoecium.*—Present both ray and disc florets.

PLANT

A. General appearance

*Height.*—Medium; 30 to 40 cm. given 2 long day weeks before pinch and lights out, and 1-3 applications 2500 B-9 after lights out.

*Branching pattern.*—Upright.

B. Foliage

*Color (abaxial).*—147A.

*Color (adaxial).*—147B.

*Shape.*—Moderately lobed.

CHART A

COMPARISON OF SPLENDOR AND SENORITA

| CULTIVAR | RAY FLORET COLOR | CAPITLUM FORM AND TYPE | BRANCHING PATTERN |
|---|---|---|---|
| SPLENDOR | LIGHT LAVENDER SMOOTH SURFACE | FLAT DAISY | UPRIGHT |
| SENORITA | LIGHT LAVENDER HAIRY SURFACE | FLAT DAISY | SEMI-SPREADING |

| CULTIVAR | DIAMETER ACROSS FACE OF CAPITULUM | PLANT HEIGHT | FLOWERING RESPONSE PERIOD |
|---|---|---|---|
| SPLENDOR | 145 to 160 mm. | MEDIUM 30 to 40 cm. | 9 week |
| SENORITA | 145 to 160 mm. | TALL 35 to 45 cm. | 10 week |

COMPARISONS MADE OF PLANTS GROWN AS A PINCHED, DISBUDDED POT MUM IN SALINAS, CALIFORNIA

I claim:

1. A new and distinct cultivar of *Chrysanthemum morifolium,* Ramat., plant known by the cultivar name of Splendor as described and illustrated, and particularly characterized as to uniqueness by the combined characteristics of flat capitulum form; daisy capitulum type; light lavender ray floret color; diameter across face of capitulum ranging from 145 to 160 mm. at maturity; uniform nine (9) week flowering response; medium plant height and upright branching pattern.

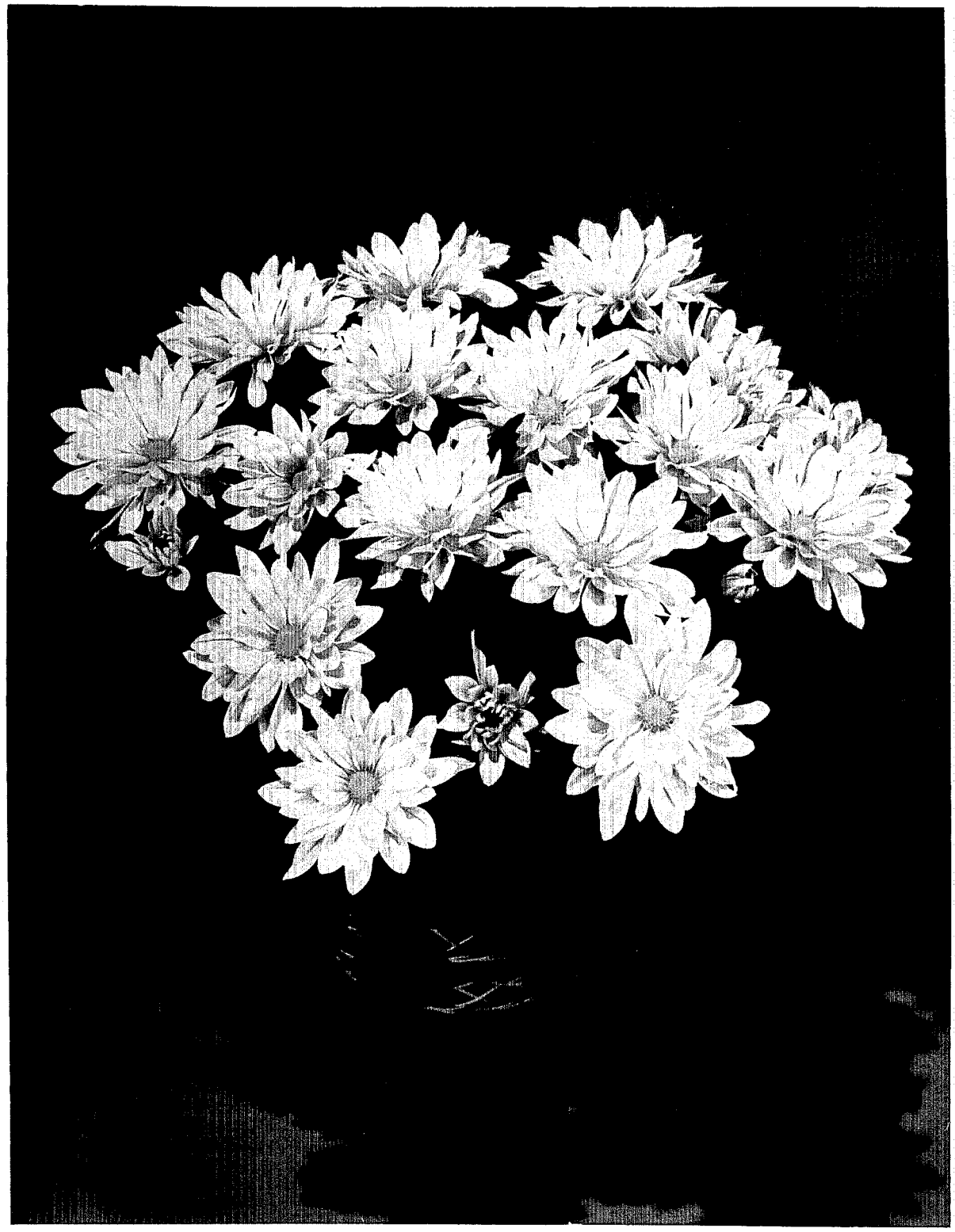

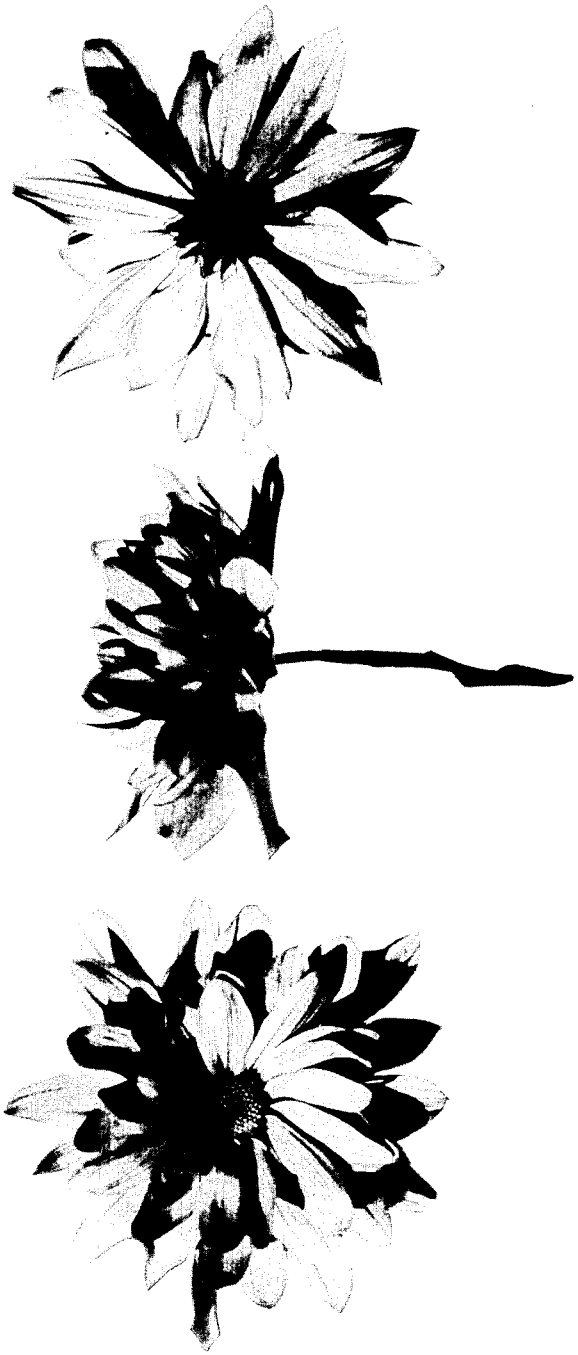

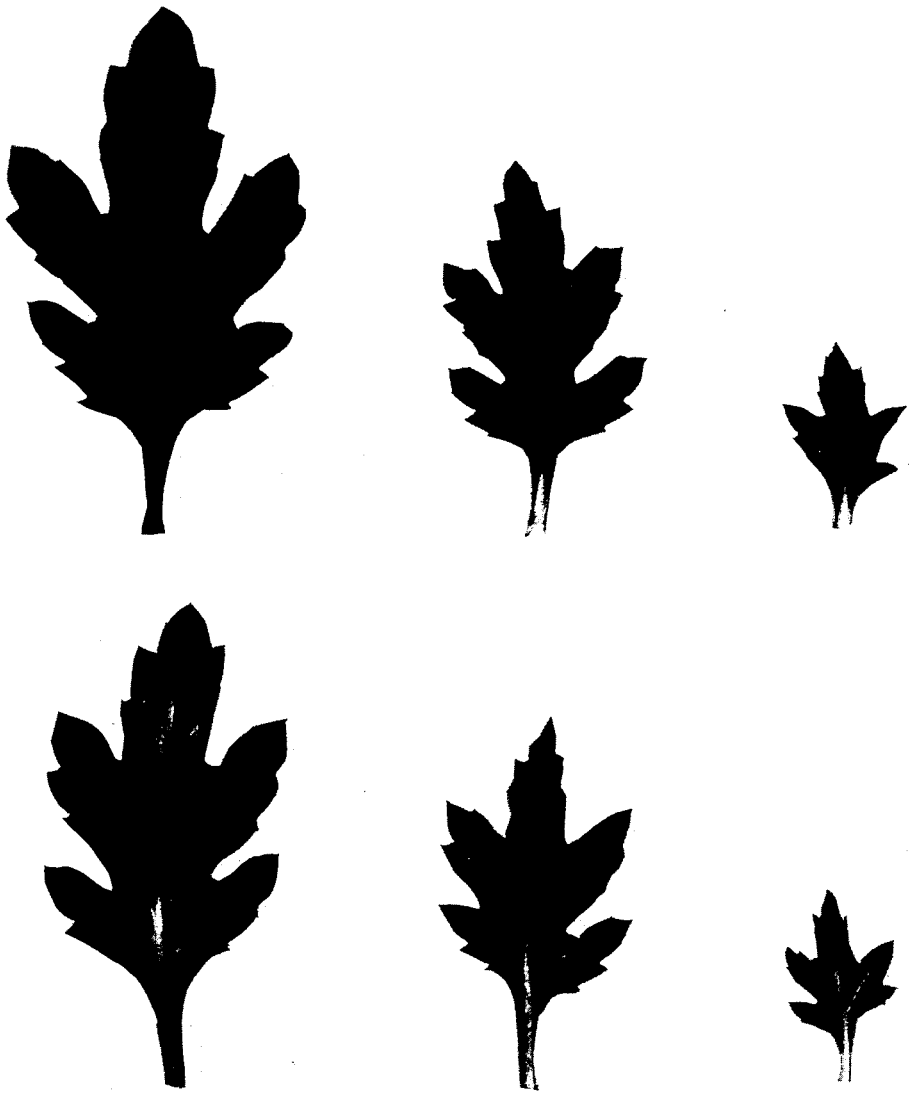

* * * * *